(12) United States Patent
Karakaya et al.

(10) Patent No.: US 10,006,846 B2
(45) Date of Patent: Jun. 26, 2018

(54) AEROSOL SENSOR AND SENSING METHOD

(71) Applicant: KONINKLIJKE PHILIPS N.V., Eindhoven (NL)

(72) Inventors: Koray Karakaya, Eindhoven (NL); Declan Patrick Kelly, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days. days.

(21) Appl. No.: 15/316,926

(22) PCT Filed: Jun. 4, 2015

(86) PCT No.: PCT/EP2015/062480
§ 371 (c)(1),
(2) Date: Dec. 7, 2016

(87) PCT Pub. No.: WO2015/189089
PCT Pub. Date: Dec. 17, 2015

(65) Prior Publication Data
US 2017/0097294 A1    Apr. 6, 2017

(30) Foreign Application Priority Data
Jun. 10, 2014  (EP) .................................. 14171789

(51) Int. Cl.
*G01N 21/00* (2006.01)
*G01N 15/06* (2006.01)
(Continued)

(52) U.S. Cl.
CPC ......... *G01N 15/06* (2013.01); *G01N 15/0205* (2013.01); *G01N 29/12* (2013.01);
(Continued)

(58) Field of Classification Search
CPC ........ G01N 15/06; G01N 15/02; G01N 29/12; G01N 33/00; G01N 21/65; G01N 21/54; A24F 47/00
See application file for complete search history.

(56) References Cited

U.S. PATENT DOCUMENTS 7,111,496 B1 *  9/2006  Lilienfeld .............. G01N 21/51
                                                        356/338
2009/0039249 A1   2/2009  Wang
2010/0315638 A1  12/2010  Goohs

FOREIGN PATENT DOCUMENTS

WO         2013064157 A1    5/2013

OTHER PUBLICATIONS

W.A. Verloop, "Resonant Air Quality Sensor", Master's Thesis, Delft University of Technology, Aug. 2013.
(Continued)

*Primary Examiner* — Abdullahi Nur

(57) ABSTRACT

A sensor system is provided for measuring particle concentration and mass concentration in an aerosol. An optical sensor (33) is used for measuring a particle concentration and a mechanical sensor (32) is used for measuring a mass of collected particles. A particle concentration in the aerosol is monitored using the optical sensor (33), until detection of a particle generating event. Upon detection of a particle generating event, a mass measurement using the mechanical sensor (32) is performed and the mass measurement is used to calibrate the optical sensor (33). This approach enables the lifetime of the mechanical sensor to be extended, because it is only used when events are detected. The optical sensor, which typically is less accurate for mass sensing, is calibrated by the mechanical sensor.

15 Claims, 5 Drawing Sheets

(51) Int. Cl.
*G01N 15/02* (2006.01)
*G01N 29/12* (2006.01)
(52) U.S. Cl.
CPC ............... *G01N 2015/0693* (2013.01); *G01N 2291/028* (2013.01); *G01N 2291/02408* (2013.01)

(56) References Cited

OTHER PUBLICATIONS

Dao Liang, Wen-Pin Shih, Chuin-Shan Chen, and Chi-An Dai, "A Miniature System for Separating Aerosol Particles and Measuring Mass Concentrations", Sensors (Basel) 2010, 10(4), 3641-3654 Published online Apr. 12, 2010. doi: 10.3390/s100403641.

L E Helseth, "Optical fibre spectrometer combined with a magnetic resonance sensor for multiple depth monitoring", Measurement Science and Technology 24, 085605, 2013. doi:10.1088/0957-0233/24/8/085605.

H.S. Wasisto, S. Merzsch, E. Uhde, A. Waag and E. Peiner, "Partially integrated cantilever-based airborne nanoparticle detector for continuous carbon aerosol mass concentration monitoring", J. Sens. Sens. yst., 4, 111-123, 2015.

\* cited by examiner

500nm        10um

500nm        10um    500nm        10um

AEROSOL SENSOR AND SENSING METHOD

This application is the U.S. National Phase application under 35 U.S.C. § 371 of International Application No. PCT/EP2015/062480, filed on Jun. 4, 2015, which claims the benefit of International Application No. 14171789.2 filed on Jun. 10, 2014. These applications are hereby incorporated by reference herein.

FIELD OF THE INVENTION

The invention relates to the measuring of particle concentration and mass concentration within an aerosol.

BACKGROUND OF THE INVENTION

Airborne particle pollution, especially particle matter size less than 2.5 μm diameter range (named "PM2.5"), is a big concern for countries like China, where the speed of industrialization stretches the boundaries of regulatory requirements.

As a consequence of increasing consumer empowerment, the demand for information about the air quality of living spaces is increasing. Especially in China, excessive PM2.5 pollution has become a common problem in the last decade. This problem is also validated by continuous measurements in various Chinese cities. The data is publicly available and can be simultaneously monitored by mobile phone applications or through the web.

Availability of this data as well as continuous national and international media attention has created strong consumer awareness about the problem.

Official outdoor air quality standards define particle matter concentration as mass concentration per unit volume (e.g. $\mu g/m^3$). The average PM2.5 pollution concentration in mainland China has been calculated based on satellite data, and it has been found that the majority of the country exceeds the World Health Organization limits of 10 $\mu g/m^3$, with some regions reaching and even exceeding PM2.5 concentrations of 100 $\mu g/m^3$.

Standardized reference measurement methods are based on measuring the mass of deposited or captured particles per air sampling volume for example using a quartz crystal microbalance, a tapered resonator, an impactor, or weighing filters and sieves.

However, these systems require professional operational guidelines for handling the manual part of the measurement (e.g. weighing a filter and sieve) and/or periodic maintenance for cleaning the accumulated mass, maintaining various system components and calibration.

Resonance based mass sensing for aerosol contamination monitoring has been proposed. For example, use of a micromachined silicon cantilever device with a picogram level of mass resolution for personal exposure monitoring has been proposed. Filters can be used for eliminating large particles and an electrostatic sampler can be provided for depositing nanoparticles on the cantilever. For example WO 2013/064157 discloses a MEMS based resonant particle measurement device, designed for measuring aerosol nanoparticles in an air flow stream.

Mechanical sensors which operate based on resonance operate in a range where the added mass is small compared to the initial resonator mass. However, continuous mass accumulation during the lifetime of the sensor is inevitable. This problem is more pronounced for MEMS scale devices, in which mechanical and/or chemical cleaning of the accumulated mass is not possible—at least for consumer applications. This gives the sensor a limited lifetime.

Optical sensors are also known. These do not suffer from the same drawback of limited lifetime, but they are less able to give information relating to particle mass.

There is therefore a need for a personal mass sensor which can be designed to have a longer lifetime and give accurate mass readings.

SUMMARY OF THE INVENTION

The invention is defined by the claims.

According to an embodiment of the invention, there is provided a sensor system for measuring particle concentration and mass concentration in an aerosol, comprising:
  an optical sensor for measuring a particle concentration and optionally the particle size distribution;
  a mechanical sensor for measuring a mass of collected particles; and
  a controller adapted to:
  monitor the particle concentration and optionally the particle size distribution in the aerosol using the optical sensor, until detection of a particle generating event;
  upon detection of a particle generating event, perform a mass measurement using the mechanical sensor; and
  use the mass measurement to calibrate the optical sensor.

The aerosol may be air or any other gas with entrained particles.

This sensor system enables accurate mass measurement using a mechanical sensor, for example a mechanical sensor which detects a change in resonance frequency. However, the operation of this sensor is not continuous so that the lifetime can be extended. Instead, the mass measurement by the mechanical sensor is triggered by detection of a particle generating event. This event can cause a rapid increase in particle concentration, or can give rise to detection of a specific particle size. For example, the particle generating event may comprise smoking, cooking, combustion processes, diffusion of external aerosols in case of opening a window, etc. In this way, the mechanical sensor can be used with a low duty cycle and is only exposed to the particulate aerosol during the sensing operation using the mechanical sensor. The need to clean the mechanical sensor can thus be avoided. A drift in accuracy of the optical sensor can be prevented by calibrating each time a mass measurement is carried out.

In an embodiment of the invention, the mechanical sensor may comprise:
  a sensing element;
  a transducer adapted to drive the sensing element into resonance and detect a resonance frequency of the sensing element, wherein the resonance frequency is dependent on a mass of particles deposited on the sensing element.

The mechanical sensor in this case is a resonant mass sensor which detects changes in resonance frequency. This may for example comprise a MEMS (micro electro mechanical system) sensor.

The controller may be further adapted to derive a volume of aerosol which has been sampled during the mass measurement, and thereby derive a mass concentration of particles per unit volume.

This enables conversion of the sensed mass into a mass concentration.

The controller may be further adapted to monitor the aerosol using the optical sensor, until a stable post-event particle concentration is recorded, and calibrate the optical sensor to form a post-event baseline using mass information from the mechanical sensor. For example, the calibration may use a post-event optical sensor measurement and a post-event mass measurement, to realign the optical sensor and the mechanical sensor after the event which triggered the mass measurement.

This enables the optical sensor to provide more accurate readings between the particle generating events, at which time more accurate particle mass information is obtained by the mechanical sensor.

The particle concentration information can then be used more accurately to indicate the mass concentration of particles while the optical sensor is being used instead of the mechanical sensor.

The optical sensor preferably comprises an optical detection system based on light scattering such as a nephelometer.

This is a readily available component which can be used within the overall system. Alternatively, a specifically designed optical unit may be used. The problems of measurement accuracy resulting primarily from particle size estimation and particle concentration to mass concentration conversion are addressed by the periodic calibration based on an actual measured mass.

In an embodiment, a sample intake device may be provided for operating during the sensing cycle of the mechanical sensor to drive the aerosol being monitored towards the sensor element. The sample intake device may comprise a fan or an electrostatic attraction arrangement, or else a thermophoretic or gravitational based system may be used.

In an embodiment, a particle filtration arrangement may be provided for selecting a range of particle sizes for which the aerosol particle concentration and mass concentration are to be measured. This means the analysis is carried out only for a range of particle sizes of interest. For example, the filtration arrangement may ensure that large particles are prevented from reaching the mechanical sensor. For example a filtration arrangement may capture particles greater than a size threshold such as 2.5 µm, for PM2.5 measurement.

The lowest resolution of the mechanical sensor may for example lie in the picogram to microgram range.

In an embodiment, a sensor that provides chemical information of the ambient may also be used for providing additional information about the particle generating event. For example, a rapid increase of certain volatile organic compounds may be associated with specific events like cooking, smoking, etc. This provides another way to trigger an accurate mass measurement using the mechanical sensor.

The controller may comprise a memory which stores a mapping between historical measurements derived from the optical sensor and corresponding historical mass measurements by the mechanical sensor. This mapping can be used to avoid unnecessary operations of the mechanical sensor, for example by recognizing that certain particle size distributions are known to correspond to certain events. This is of particular interest when there are repeating events, for example cooking events.

In an embodiment of the invention, there is also provided a method for measuring aerosol particle concentration and mass concentration, comprising:
    monitoring the aerosol using an optical sensor by measuring a particle concentration and optionally the particle size distribution;
    detecting a particle generating event based on the measured particle concentration and optionally the size distribution;
    in response to detection of the particle generating event, performing a mass measurement of collected particles using a mechanical sensor; and
    using the mass measurement to calibrate the optical sensor.

This method enables accurate mass measurement using a mechanical sensor with extended lifetime as explained above.

As outlined above, the aerosol may be monitored using the optical sensor, until a stable post-event particle concentration is recorded, and the optical sensor can then be calibrated to form a stable baseline. The calibration may comprise correlating particle concentration information from the optical sensor with mass information from the mechanical sensor. This provides a calibration based on stable values after the event has completed.

A mapping may be stored between historical particle concentration measurements by the optical sensor and corresponding historical mass measurements by the mechanical sensor. This means that a mass measurement can be avoided if there is already stored data that can be used. Thus, the stored mapping may be used to inhibit performing a mass measurement after detection of a particle generating event if there is a mapping to a historical mass measurement. This further enables the lifetime of the mechanical sensor to be extended.

The stored historical mass measurement may be scaled using the optical sensor measurement to provide a mass indication. Thus, the mapping may relate to the particle distribution characteristics rather than the absolute concentration.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a sensor system for measuring particle concentration and mass concentration in an aerosol. An optical sensor is used for measuring a particle concentration and optionally the size distribution, and a mechanical sensor is used for measuring a mass of collected particles. The particle concentration (and optionally size distribution)

in the aerosol is monitored using the optical sensor until detection of a particle generating event. Upon detection of the particle generating event, a mass measurement using the mechanical sensor is performed and the mass measurement is used to calibrate the optical sensor. This approach enables the lifetime of the mechanical sensor to be extended, because it is only used when events are detected. The optical sensor, which typically is less accurate for mass concentration determination, is calibrated by the mechanical sensor.

Direct mass measurement using resonant devices is a known technique. It is based on the relationship between the resonance frequency ($f_0$) and the mass of a resonator, as shown in FIG. 1.

Figure 1:
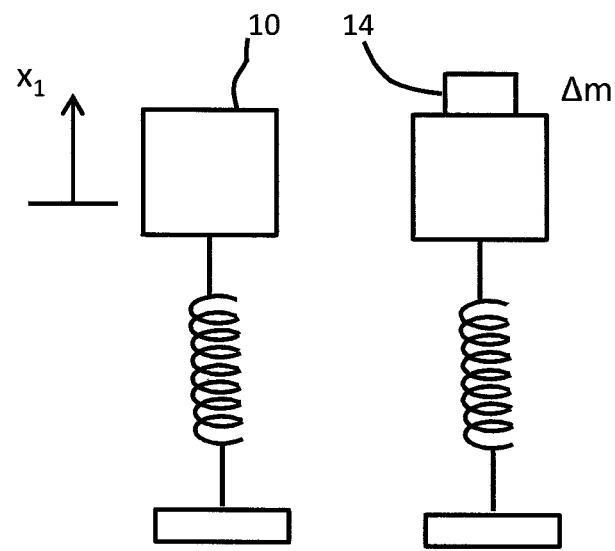
FIG. 1 shows the fundamental aspects of a resonance based mass detection, explained with a spring-mass system, where the mass of the resonator sensor influences the resonance frequency.
Figure 1:
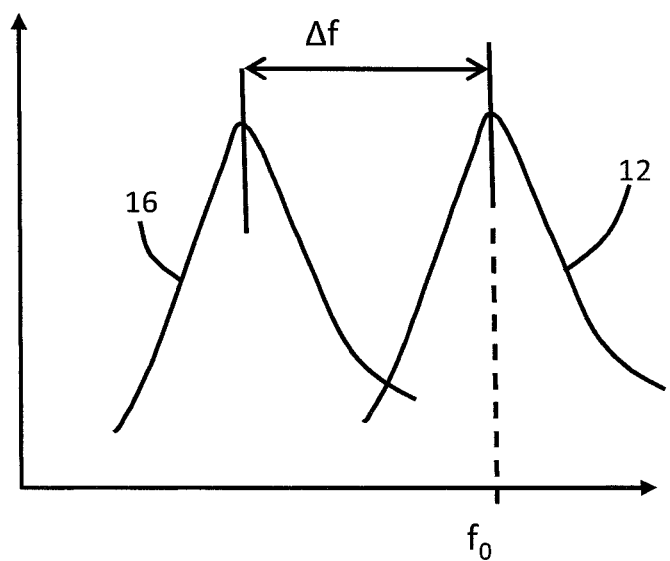

In FIG. 1, a resonator mass 10 is represented schematically, with a mass m and spring constant k. The graph shows the amplitude of the resonant oscillations (on the y-axis) as a function of frequency (the x-axis). Plot 12 is for the basic resonator mass. If an additional mass 14 is added ($\Delta m$), the oscillation curve shifts down in frequency to plot 16 with a frequency shift $\Delta f$.

The equations which govern the resonant vibrations are;

$$f_0 = \frac{1}{2\pi}\sqrt{\frac{k}{m}} \quad (1)$$

$$\Delta f = -\frac{1}{2}\frac{\Delta m}{m}f_0 \quad (2)$$

$$\Delta m_{min} \propto \frac{m}{Q} \quad (3)$$

Equation 1 shows the relationship between the basic resonance frequency and the resonator characteristics. Equation 2 shows the change in frequency caused by a change in mass, and equation 3 shows the minimum mass ($\Delta m_{min}$) that can be detected. The minimum depends on the mechanical quality factor Q of the resonator.

There are several examples of resonance based mass sensing for aerosol contamination monitoring in literature. For example, use of a micromachined silicon cantilever device with a picogram level of mass resolution for personal exposure monitoring has been proposed. Filters can be used for eliminating large particles and an electrostatic sampler can be provided for depositing nanoparticles on the cantilever.

For example WO 2013/064157 discloses a MEMS based resonant particle measurement device, designed for measuring aerosol nanoparticles in an air flow stream.

As a rule of thumb, mechanical sensors which operate by monitoring changes in resonance frequency operate in a range where the added mass is small compared to the initial resonator mass. However, continuous mass accumulation during the lifetime of the sensor is inevitable. This problem is more pronounced for MEMS scale devices, in which mechanical and/or chemical cleaning of the accumulated mass is not possible—at least for consumer applications. Therefore, the lifetime of a MEMS sensor can be roughly estimated by considering the initial mass and the approximate mass deposition per measurement cycle.

A brief calculation is given below, as an example for a silicon MEMS cantilever:
Dimensions: 100 μm width, 1000 μm length, 10 μm thick
Volume: $10^6$ μm$^3$
Mass: 2650 ng (silicon density 2.65 g/cm3)

For a minimum particle concentration detection limit of 10 μg/m$^3$ (World Health Organization limit for annual mean concentration), and a sample air volume of 1 liter (1 min sampling with 1 l/min air intake), 10 ng of mass deposition on the resonator is a reasonable estimate. For increasing concentrations, the mass deposition increases proportionally. This results in a number of measurement cycles to double the original mass of the resonator which depends on the concentration ranges, as summarized below:

| PM 2.5 concentration (μg/m$^3$) | Absolute mass per sampled volume of 1 liter (ng) | Number of cycles (#) |
|---|---|---|
| 10 | 10 | 265 |
| 20 | 20 | 132 |
| 50 | 50 | 53 |
| 100 | 100 | 26 |

The PM2.5 concentration can reach several hundreds of μg/m$^3$ (e.g. 700 μg/m$^3$ in Beijing, Jan. 13, 2013), so that an even shorter lifetime can result, which is not appropriate for using such systems at consumer level applications. When the particle accumulation on the resonator pushes the sensor resonance frequency out of the drive or read-out circuit bandwidth, the sensor reaches its end of life.

This mass accumulation also pushes the resonance frequency to lower values, where the quality factor is lower, so that the mass resolution also decreases gradually with age. The mass accumulation also changes the surface structure of the resonator so that the particle deposition characteristics vary over in time. If a continuous layer is formed, this also alters the stiffness of the resonator, hence changes the resonance frequency. The conductivity of the sensor can also change which hinders deposition efficiency in the case of electrostatic particle collection.

In addition to the collection of mass leading to limited lifetime, there are a number of other problems relating to resonance-based mass measurement which may lead to limited lifetime. For example, the filters in the sampling subsystem can become clogged and their filtration efficiencies degrade over time.

Optical sensing technologies (for PM2.5) have also been proposed for consumer level applications for air purifiers. The primary technology for consumer level applications is based on the optical scattering by suspended particles in air (e.g., nephelometry). Nephelometers use a light source and an optical detector. The method is essentially based on measuring the scattered light intensity by suspended particles in air (or other carrier gas).

Although light scattering is a well-established particle measurement technique, it also has fundamental limitations. Optical sensors based on light scattering are calibrated for a certain type of aerosol type and composition and their accuracy may vary dramatically depending on a number of factors including particle shape, optical properties of particles, particle density, etc. The output gives particle density information for the range of particle sizes which are detected but it does not give particle mass information, or particle distribution information (without further signal analysis as discussed below).

The particle size range is typically from 200 nm up to 50 μm in diameter. This large particle range may also cause large deviations in measurement accuracy, as reflectance from large and small particles can vary significantly.

The reflected light intensity can also be affected by the particle shape, so that significant differences in particle shape (e.g. spherical vs. acicular) can cause deviation from an accurate measurement. The particle density can also influence the accuracy, particularly, when converting from particle concentration to mass concentration, and vice versa. Typically, particle mass information is desired, since the regulatory limits are based on mass concentration values.

The particle chemistry also influences the sensor response. In an indoor ambient environment, a variety of particle types may be present; cooking-originated pollutants, candle flame, cigarette smoke, diffused-in outdoor pollutants, allergens, etc. Nephelometry gives no information about the nature of suspended particles. It should be noted that particle chemistry, in combination with particle physical characteristics (color, roughness, etc.), may also affect the reflection/absorption of light through the particle surface and has an influence on measurement accuracy.

The sampling volume, hence the concentration, is dictated by the air flow in the measurement compartment. Compact nephelometers use a heater for utilizing a chimney effect for delivering the sample air, whereas some models also use fans for delivering the sample air. All possible variations that may affect the air flow rate, and will lead to erroneous readings in particle concentration.

There are therefore disadvantages to mechanical sensors based on measurement of resonant frequency as well as disadvantages to optical systems. Optical systems for example give uncertainty to the particle number detection, as well as the particle number to mass conversion, which is the unit used in indoor air quality standards.

The invention provides a hybrid solution, for combining the advantages of the two techniques. The two systems are combined in a way which gives greater reliability and enables no or low maintenance, as well as low cost particle analysis. This makes the sensor system suitable for consumer level applications, such as air purifiers, stand alone air sensors, or other air treatment devices such as air conditioners incorporating an air quality sensing function.

In particular, by combining simultaneous and/or sequential operation of the different types of sensors, two major problems can be addressed. The lifetime of the mechanical sensor can be prolonged by means of duty cycling, while providing particle concentration information with nephelometers. Event-based calibration of nephelometer type sensors is enabled to provide more accurate particle characterization.

The benefits of duty cycling for mechanical sensors in terms of lifetime enhancement are clear. Instead of a continuous operation, the sensor system can respond only to different events that generate different types of particles; e.g. cooking, burning candles and incense, action of different aerosol sprays (e.g., home cosmetics), outdoor originated particles, etc.

Figure 2:
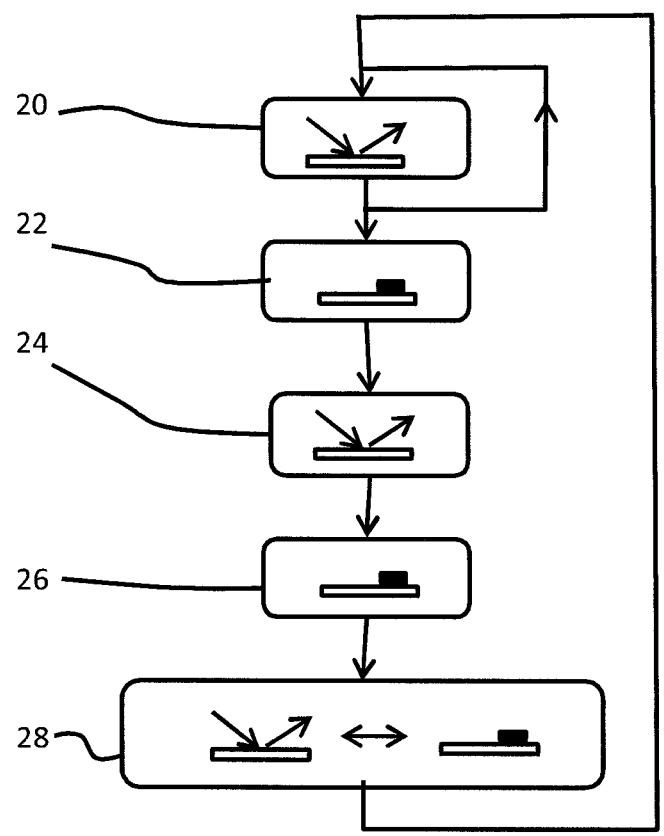
FIG. 2 shows an embodiment of the method of the invention.

FIG. 2 shows an example of the method of the invention.

In step 20, the optical sensor (e.g., nephelometer) monitors the particle concentration and optionally also the particle size distribution. This continues until a particle generating event is detected, based on the measured particle concentration. This event is, in the most simple case, a steep increase in particle concentration. However, other indicators can be used to recognize the particle generating event, such as a volatile organic compound (VOC) sensor detecting a sharp increase in the VOC level and/or any other connected sensors or connected data sources providing a trigger indication. Examples are meteorology information, location and traffic data, and window sensor status (e.g., open or closed).

In response to detection of the particle generating event, a mass measurement of collected particles is carried out in step 22 using a mechanical sensor, such as a mechanical sensor which operates by detecting changes in resonance frequency. This involves the mechanical sensor starting sampling and measuring mass concentration.

The process waits after step 22 for the end of the event, as determined by the optical sensor (which continues to monitor) or by the external input.

After the end of the event, the optical sensor can be used to measure a post-event concentration value in step 24. This is optional, in that the last optical reading can instead be used.

Also, after the end of the event, the mechanical sensor can be used to measure a post-event mass value in step 26.

The mass measurement of step 26 is correlated with the particle concentration from the optical sensor measurement of step 24 to calibrate the optical sensor. This calibration takes place in step 28. This means the accuracy of the optical sensor is maintained for the subsequent optical measurements.

The direct mass measurement enables calibration of the optical sensor, by resetting the relationship between the concentration measured by the optical sensor and the corresponding mass.

The optical sensor typically provides a particle concentration measurement, as a number of particles per unit volume. This can for example be achieved by detecting individual particles, so that each signal represents a single particle. The volume of sample analysed thus yields a particle concentration figure. The optical sensor can for example give particle size information by discriminating between the signal for different particles. In one example the optical sensor is based on light scattering that can use scattered light intensity differences to distinguish different particle sizes. Thus, an optical sensor can give information about particle count (i.e. concentration for a known sample volume) and particle size.

By providing this size information in bins, the particle concentration for bands of particle size can thus be derived. The optical sensor does not however measure mass concentration (i.e. particle mass per unit volume). Without a direct mass measurement, the calculation of the mass concentration from the optical measurement is an estimate. By identifying events and providing direct mass measurements for those events, the estimates can be based on actual measurements.

The optical sensor measurement is based on the scattered light and its accuracy is directly proportional to the scattered light intensity. Over time, the brightness of the light source used by the optical sensor (for example an LED) decreases, and this gives rise to sensor drift. There is also an issue with contamination, which is more pronounced for indoor aerosols, especially oily aerosols which may form a layer on various optical components of the system (lenses, LED surface, etc.). This results in a decrease in the light intensity, hence false measurements.

The optical sensor may give concentration and size range information as explained above, and this provides a distinctive profile for a particular event.

The purpose of the calibration is to improve the accuracy of a particle concentration to particle mass concentration conversion.

In this way, the mechanical sensor only operates for a very limited time and the continuous measurement is carried out by the optical sensor. Additionally, inaccurate particle concentration to mass concentration conversion of the optical sensor measurements are also prevented by providing an event based calibration for optical sensor measurements.

In the case of outdoor operation, the sensor data can be correlated for traffic events (e.g., peak hours and low traffic hours), social events (e.g. fireworks), meteorological conditions (e.g., rain, wind direction, season), environmental factors (e.g. desert dust) or other urban local information (e.g. building and road constructions) by using appropriate sensors and/or combining the sensor operation with other publicly available data.

The detailed design of the sensor will depend on the application conditions.

Figure 3:
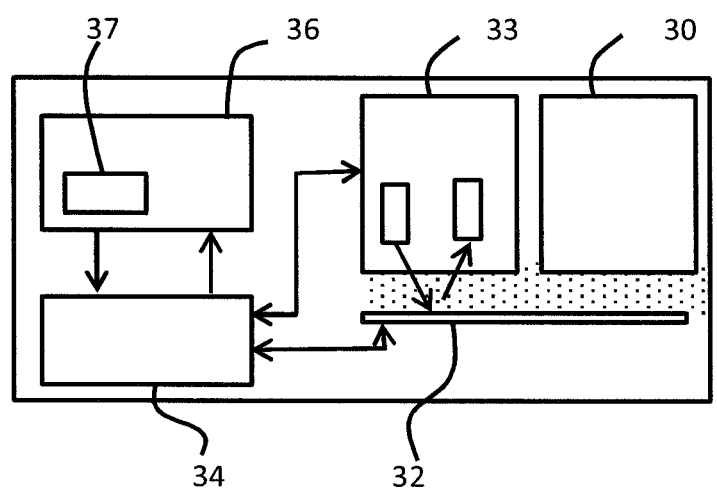
FIG. 3 shows an embodiment of the sensor of the invention.

In general, as shown in FIG. 3, the sensor system comprises a particle pre-classification unit and intake sampling device 30 (e.g. a filter stack), a mechanical sensor 32 which in this example comprises a MEMS resonator 32 (described below), and an optical sensor 33 which in this example comprises a nephelometer. An electronic circuit 34 is provided for driving and reading out the sensors and other system components, and a controller 36 is provided for data processing and storage. Air flow to the sensor unit (i.e. intake sampling) can be handled by using fans and/or thermal convection.

The sample intake and conditioning unit 30 is designed taking into account the targeted particle range. A specific particulate matter range (e.g. PM1, PM2.5, PM10) may be targeted by using appropriate particle size pre-filtering to remove larger particles e.g. using a mesh or fibrous filter combination or inertial/aerodynamic separation. By providing this type of pre-filtering operation, it can in particular be prevented that large particles reach the mechanical sensor, thereby prolonging the lifetime.

Deposition of the particles can be controlled by electrostatic or electrophoretic precipitation of charged particles on a grounded or oppositely biased resonator. Thermophoretic precipitation may instead be used which comprises creating a temperature difference between the resonator and a counter surface. The deposition may instead be based on random particle movement. A fan or pump for delivering the sampled air volume may also be used.

The selection depends on the minimum detectable mass, average particle concentration in 'clean air' (i.e., baseline level), ratio of particles passing through the particle filters in the sampling subsystem and eventually the user requirements for minimum particle concentration detection.

A MEMS resonator may be used as the mechanical sensor 32. The resonator can be designed and fabricated with suitable dimensions to achieve the desired resonance frequency for providing the required limit of detection.

Examples of possible resonator structures are cantilevered structures (one end clamped, other end free), as well as double-clamped or membrane type resonators.

A cantilevered design may be of particular interest for providing sufficient electric field density at the cantilever tip in the case of electrostatic particle collection. A cantilevered structure can be in simple rectangular form, in triangular form (for a larger clamping area) or in hammerhead-like form for increasing the surface area while maintaining the low area at the clamped end.

These parameters all affect the resonance behavior of the system and basic resonator design principles can be used.

The circuitry 34 for driving and reading out the resonance frequency also depends on the Q-value of the resonator, choice of transducer (e.g. piezoelectric, thermal, piezoresistive, optical, capacitive, etc.). Depending on the requirements for minimum detectable mass, a Q-compensation mechanism may be implemented for increasing the mass resolution of the system. The detection of the resonance frequency in the electronic domain is selected to be suitable for the actuation method. Fundamentals of circuit design for such resonators are known in literature.

For example, in the case of piezoelectric actuation and sensing, an oscillator circuit is used which incorporates the electrical impedance of the resonator. In the case of electrostatic/capacitive actuation and sensing a voltage-controlled oscillator circuit is used.

The controller 36 for data processing and handling can also be selected and designed depending on the application requirements such as the data sampling rate, processing load for calculations and implementation of data processing algorithms.

As mentioned above, the algorithm can be further enhanced by a learning mechanism by incorporating the time stamp of different events for a given household.

FIG. 3 shows that the controller includes a look up table 37, which is used for the learning process. It provides a mapping between events which can be recognized from the optical sensor output (or from other trigger inputs provided to the system), and the corresponding mass values. In this way, mechanical sensor measurements can be avoided if they are already known from previous measurements.

For example, a periodic set of events recurring around the evening time can be associated with cooking and cooking originated particle sources. Once a consistent data correlation is established for cooking, the sampling frequency of the resonator can be further decreased for an even increased operational lifetime.

An example of learning mechanism will now be discussed in greater detail.

The aim is to reduce further the times when the mechanical sensor is used, for example to avoid unnecessary repetitions for the same event at different times. However, similar events (e.g. cooking) may nevertheless have different constituent particles (e.g. based on different cooking material) and therefore the same particle concentration may not correspond to the same mass so that calibration using a mass measurement is still required.

The learning mechanism can also improve the quality of the optical measurements. Variations of the optical properties of aerosols also impact on the accuracy of the optical readings. For example, aerosols with significantly different optical properties (i.e. refractive index) will result in differences in measured particle size distribution. The changes in optical properties of particles will not normally affect the overall particle concentration measurement but will have an influence on the size estimations.

A self-learning system is described below that couples the outputs of the optical and mechanical sensors, by means of a re-adjustment process.

The optical sensor typically gives only a particle concentration (based on a particle count), although analysis of light scattering signals can be used to derive particle size information as mentioned above. It is also possible to distinguish properties of particles with the same size, for example using multiple sensors for detecting different particle properties More advanced signal processing techniques have also been proposed to determine the particle size distribution from an optical scattering signal and thereby to categorize the particle according to size (e.g. PM 2.5)

By way of example, Mie theory (which is based on the Mie solution to Maxwell's equations) is used to characterize the light scattering of suspended particles.

Light diffraction particle sizing can be used to provide size distribution information, based on the property that small particles provide large angle scattering and large particles provide small angle scattering. Dynamic light scattering can be used, in which the way the intensity of scattered light varies over time is dependent on particle size. This approach is based on the velocity of Brownian motion of the suspended particles.

Thus, there are various known optical techniques for deriving particle concentration, and data processing techniques are also well known to extract particle size distribution from the optical sensor information.

One approach is to provide a fixed scattering angle (e.g. fixed optical alignment of light source, detector and optical scattering volume) and to provide comparison of the light scattering intensity as a function of the particle size. This enables a measurement system without any moving parts for sweeping over a scattering angle (i.e. a goniometer).

However, without knowledge of the particle material, these approaches do not provide mass information.

The approach described below is based on storing the characteristics of particles (such as size distribution and optionally other properties) together with a corresponding mechanical sensor value. Each time the mechanical sensor is used, the characteristics are recorded, including instantaneous values but also optionally the change over time before/after, and/or average values over a time window.

Once a set of measurements has been recorded, when the system is triggered to perform a mass measurement, it will first compare the current particle profile from the optical sensor to the stored values. If there is a match, then the system will use the stored values of the mechanical sensor to determine the current mass value.

In this way, a mass measurement can be avoided based on the recognition of the event from the optical sensor information alone and the mass measurements taken previously for the corresponding event.

The optical particle characteristics (size distribution and other characteristics) can thus be used to identify the corresponding pre-stored mass measurement if any. Then, based on the particle concentration and characteristics, the mass measurement can be determined.

The mass can be scaled according to the optical readings. For example, if the particle characteristics as determined by the optical measurement match a stored set of data, but the particle concentration is half that recorded in the stored data, then the mass measurement will be scaled to half the stored value.

Figure 4:
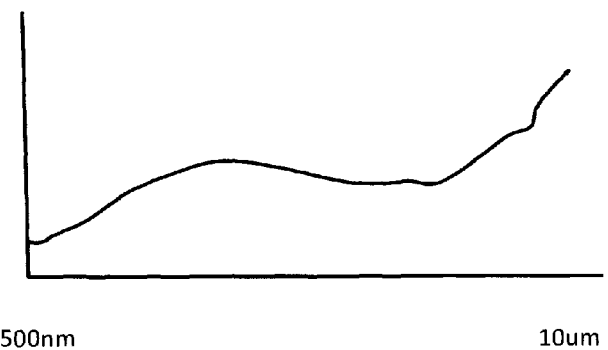
FIG. 4 shows a particle size distribution function.

FIG. 4 shows an example of a possible particle size distribution which can be measured optically.

An exact particle size distribution is not necessary, since the same type of event will give a variation in distribution. A more practical approach for obtaining particle distribution information is to collect a particle concentration in categories, which acts as a kind of averaged particle size distribution.

Figure 5:
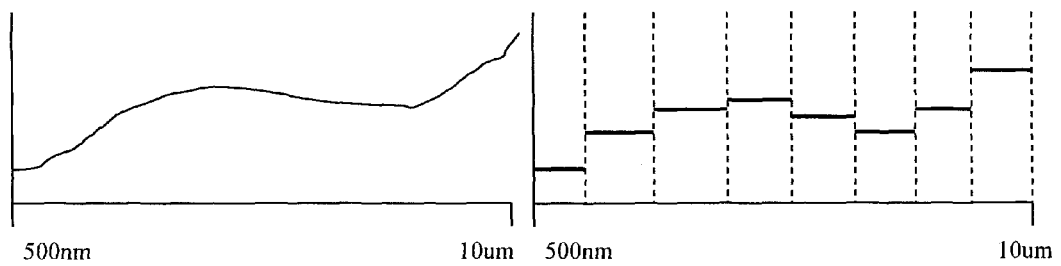
FIG. 5 shows how the function of FIG. 4 can be divided into discrete sections.

The conversion of the continuous function to a discrete function is shown in FIG. 5.

When an event is detected as discussed above, the system first determines the particle size distribution in the discrete form and addresses a stored table. If there is a match, then the system can determine the mass from the stored value.

The actual particle concentration and the stored particle concentration associated with the stored table are then used to scale the stored mass value to give the actual result.

For example, if the particle size distribution matches an entry in the table (within a certain error margin), the system can look up the recorded particle concentration and the recorded mass. Based on this, the actual particle concentration is used to determine the actual mass. In this way, the values in the table are scalable. For example, if the recorded mass is 30 μg/m$^3$ and the recorded particle concentration is 120, whereas the measured particle concentration is 80, the actual mass will be calculated as 20 μg/m3.

As mentioned above, the particle size distribution measured is not expected to match exactly but within a reasonable error level. This error level can be pre-set or can be determined form multiple mechanical sensor measurements. If the actual mass measured deviates by a certain error, the measured particle size distribution can be considered to define a different category and can then be stored as a separate entry in the table.

In order to derive the particle mass concentration from the particle concentrations in each size category, each detected event type allocates mass concentration values to each size category.

For example, for a particular event, the mass concentration for bin A may be $M_A$ g/m$^3$.

$$M_A(g/m^3) = [bin\ A\ count\ (count/m^3)] \times [bin\ A\ average\ particle\ volume\ (m^3)] \times [bin\ A\ average\ particle\ density\ \rho_A(g/m^3)]$$

The average density differs for each bin and for each aerosol source, and the aerosol source is determined by its characteristic particle size distribution for example.

The overall mass concentration is then the sum of the mass concentrations for all bins.

Figure 6:
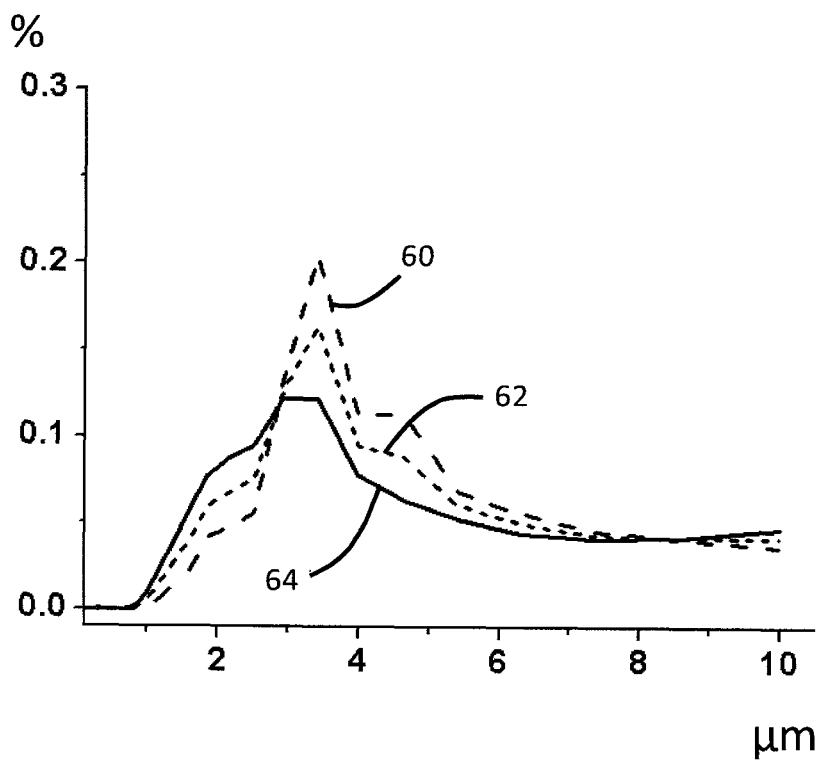
FIG. 6 shows particle density distribution functions for cooking three different food items.

FIG. 6 shows actual particle size distribution information for three cooking events as a percentage of the total.

These cooking events are stir frying meat with shallots (plot 60), stir frying shrimps (plot 62), and stir frying vegetables (plot 64). The y-axis plots the volume fraction for the particular particle size.

The x-axis shows the particle size in μm (with points every 0.5 μm). The y-axis is the proportion of the total number of particles with that size to provide normalized numbers of particles.

The table below shows the weight percentage of organic compounds in particulate organic matter generated by the three cooking situations mentioned above, quantified by gas chromatography mass spectrometry.

|  | Stir frying vegetables | Stir frying shrimp | Stir frying meat with shallot | Mixed three dishes |
|---|---|---|---|---|
| n-Alkanes | 0.30 ± 0.11 | 0.44 ± 0.14 | 0.33 ± 0.07 | 0.44 ± 0.47 |
| PAH (polycyclic aromatic hydrocarbons) | 0.01 ± 0.00 | 0.03 ± 0.03 | 0.01 ± 0.00 | 0.01 ± 0.00 |
| Saturated Fatty Acids | 11.56 ± 1.74 | 13.7 ± 1.68 | 12.9 ± 2.49 | 13.51 ± 0.34 |
| Unsaturated Fatty Acids | 85.62 ± 1.92 | 74.46 ± 4.68 | 73.29 ± 6.48 | 67.84 ± 0.68 |
| Diacid | 0.02 ± 0.01 | 0.01 ± 0.01 | 0.03 ± 0.04 | 0.01 ± 0.01 |
| 9-Oxo Nonanoic | 0.06 ± 0.03 | 0.02 ± 0.01 | 0.02 ± 0.01 | 0.01 ± 0.00 |

-continued

|  | Stir frying vegetables | Stir frying shrimp | Stir frying meat with shallot | Mixed three dishes |
|---|---|---|---|---|
| acid |  |  |  |  |
| Nonanal | 0.06 ± 0.07 | 0.04 ± 0.03 | 0.05 ± 0.05 | 0.02 ± 0.00 |
| Single glycoside | 0.02 ± 0.01 | 0.05 ± 0.04 | 0.17 ± 0.15 | 0.05 ± 0.02 |
| Steroid | 2.21 ± 0.22 | 10.38 ± 2.87 | 11.6 ± 3.27 | 14.07 ± 1.03 |
| Vitamin E | 0.15 ± 0.06 | 0.88 ± 0.28 | 1.60 ± 0.77 | 4.03 ± 0.47 |

From this table it can be seen that the composition of the particulate matter for the three dishes differs and therefore it is expected that the actual weight measurement will differ for different cooking events. Similarly, other events (with different particle density distribution profiles) will have different particle composition and therefore different mass measurements (even with the same particle concentration).

Figure 7:
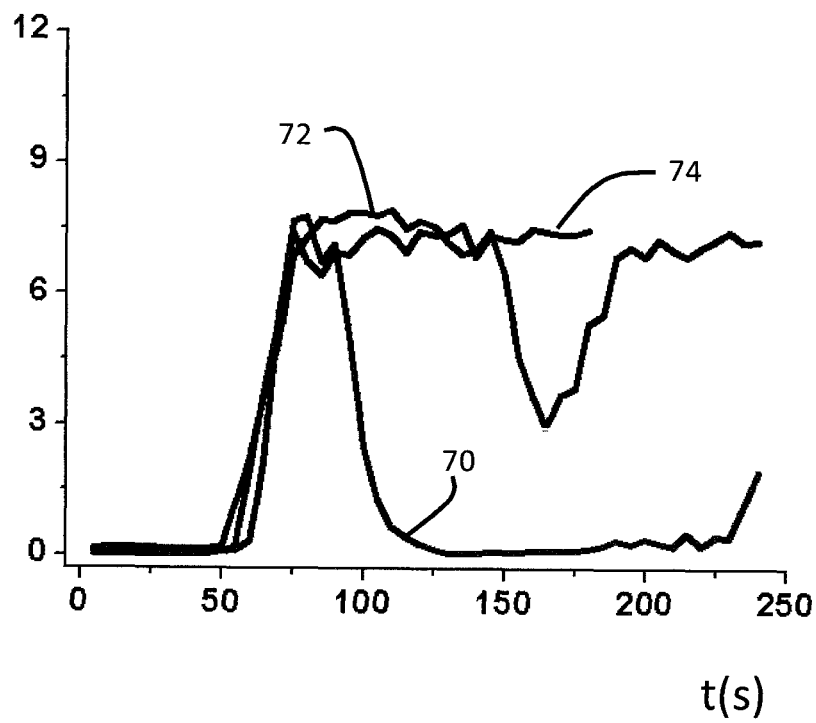
FIG. 7 shows particle mass concentration functions over time for cooking the three different food items.

FIG. 7 shows the mass concentration over time for the three cooking events.

Plot 70 relates to stir frying meat with shallots, plot 72 relates to stir frying shrimps, and plot 74 relates to stir frying vegetables. It can be seen that information relating to the evolution of the mass over time can also associated with different events.

An air treatment operation can then be optimized according to the detected types of particle.

Figure 8:
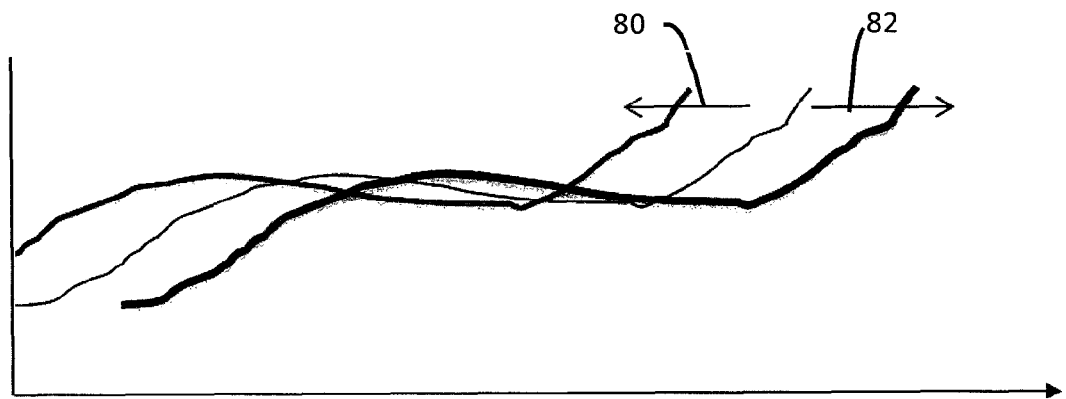
FIG. 8 shows how particle density distribution functions may be measured differently for different optical properties of particles.

FIG. 8 shows the effect of different optical properties of particles on the accuracy of the optical particle size distribution measurement. As a result of changes in refractive index, particles may scatter more or less light than the reference system, on which the calibration is based. This condition shows itself as a shift of the particle size distribution for a given event, as shown in FIG. 8. Arrow 80 shows the effect of a lower reflectivity on the particle concentration information and arrow 82 shows the effect of a higher reflectivity on the particle concentration information.

As explained above, the particle size distribution is used to distinguish different cases and link to actual mass measurements. The fact that the particle size distribution is effected by the particle properties, as shown in FIG. 8, is not a problem. As long as an event specific particle size distribution pattern is maintained, accurate particle size distribution information is not necessary, it is only used to distinguish between different events and the particle properties, of which refractive index of the particles is one property.

Figure 9:
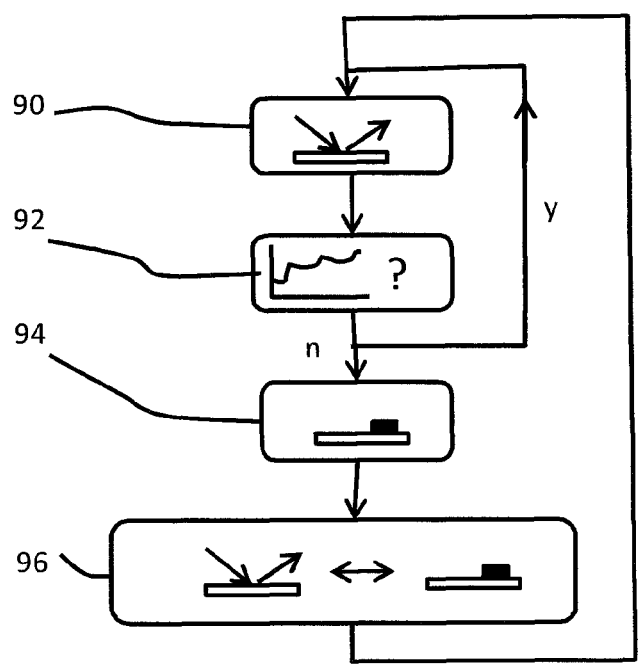
FIG. 9 shows a method of learning from previous mass measurements to reduce the number of mass measurements needed.

FIG. 9 shows an example of the method of the invention which makes use of the learning process described above.

In step 90, an optical sensor measurement is taken, until an event is detected. The event may be detected by the optical sensor itself, or it may be received as an external trigger.

In step 92, the particle distribution characteristics provided by the optical sensor are compared with the data in the look up table. If there is a match, a mass measurement can be provided from the look up table (with appropriate scaling if required) and the optical sensing can continue without the need for a mechanical mass measurement.

If the distribution characteristics do not match, a mechanical mass measurement is taken in step 94. The look up table is updated with a new event characterization in step 96 and the process returns to the optical sensing.

The particle size distribution for different events are roughly known; for example combustion processes (candles, cigarette smoke, etc.) consists of a reasonably homogeneous particle size distribution, that shows itself as the same increased trend for PM 1, PM2.5 and PM10. On the contrary, events that are related to dust (e.g. dusting, vacuum cleaning, changing bed, ironing, etc.) have a significant character with a sharp increase in PM10 but no change at PM1 and PM2.5.

The calibration involves calibrating particle concentration to mass concentration conversion factors. Different events generate particles with different optical properties, and densities, which induce errors for the particle concentration to mass concentration conversion.

Once an event is identified (e.g. smoking), for a given ambient atmosphere (i.e. the room that the sensor is placed in), the previously stored (learned) particle concentration to mass concentration conversion factors can then be used for that event. Thus, the calibration involves updating a mapping between particle concentration and mass concentration, and in respect of specific detected events.

Different events will give rise to particles of very different properties. Even if particles have the same size range they may have very different optical properties, for example soot and sand. The particle concentration may be the same, whereas there are very different mass concentrations. By mapping the characteristics of an event to stored values, it becomes possible to attribute appropriate conversion factors so that the particle concentration (count per $m^3$) is accurately converted to mass concentration ($mg/m^3$). The calibration factors essentially convert from number of particles (count) to mass, i.e. they provide a mass per particle factor for different types of particle generating event.

As explained above, the calibration is performed based on detected events. However, in the absence of events, a calibration may also be performed periodically, for example daily.

The calibration should be not too frequent in order to maintain the lifetime of the mechanical sensor. The overall lifetime should exceed a guarantee period such as 1 to 3 years.

The particle concentration to mass concentration conversion for the optical sensor may fail for different events; e.g. the conversion factor used for cigarette smoke may not be useful for conversion factors for traffic induced aerosols. The self learning system described above can adapt to changing environmental conditions associated with different aerosol generating events.

The drift caused by light source aging is somewhat predictable but drift due to contamination of optical components is random. The hybrid approach means the right measurement is available at all times.

The invention makes use of a particle generating event to trigger a mass measurement. This may be detection of a particular particle concentration or detection of a particular particle size. Preferably, the particle generating event is an event which can be detected by the optical sensor. Furthermore, the mass measurement may be carried out periodically if no event is detected for a particular time period, so that the optical sensor can be calibrated periodically even before an event is detected which triggers the more accurate mass sensing operation.

The invention is applicable to air purifiers, stand-alone particle sensor units, personal exposure monitoring devices, vehicle cabin particle measurement sensors, particle sensors for outdoor use (as a standalone sensor unit or for example, sensors for lamp posts for city management), ventilation units, various parts of a building climate management system and in general various types of mechanical sensor which operate by detecting changes in resonance frequency. There are also medical applications in respiratory support and drug delivery applications.

The examples above are based on detection of PM2.5 particles, but the invention can be applied to PM10, PM1 particles or other categories of ultrafine particles.

The example above is based on a MEMS resonator. However, the approach can be based on other micro resonators, for example a membrane device (similar to a capacitive micromachined ultrasound transducer) or a quartz crystal microbalance (QCM). The resonator may be a bulk acoustic wave (BAW) resonator, or a surface acoustic wave resonator (SAW).

The sensor system may further comprise a chemical sensor for providing information about the particle generating event. This may for example be a VOC sensor, for providing the event trigger to prompt the taking of a mechanical sensor reading. The event triggering may be based on a number of possible inputs, including the chemical sensor, external inputs and the optical sensor.

The system makes use of a controller. Components that may be employed for the controller include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform at the required functions. Various storage media may be fixed within a processor or controller or may be transportable, such that the one or more programs stored thereon can be loaded into a processor or controller.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A sensor system for measuring particle concentration and mass concentration in an aerosol, comprising:
   an optical sensor for measuring a particle concentration and a particle size distribution;
   a mechanical sensor for measuring a mass of collected particles; and
   a controller adapted to:
   monitor, via the optical sensor, the particle concentration and the particle size distribution in the aerosol until a particle generating event corresponding to a particular combination of particle concentration and particle size range information is detected;
   perform, via the mechanical sensor, a mass measurement only in response to detecting the particle generating event; and
   calibrate the optical sensor with use of the mass measurement.

2. The sensor system as claimed in claim 1, wherein the mechanical sensor comprises:
   a sensing element; and
   a transducer adapted to drive the sensing element into resonance and to detect a resonance frequency of the sensing element, wherein the resonance frequency is dependent on a mass of particles deposited on the sensing element.

3. The sensor system as claimed in claim 1, wherein the controller is further adapted to derive (i) a volume of aerosol sampled during the mass measurement, and (ii) a particle concentration per unit volume.

4. The sensor system as claimed in claim 1, wherein the controller is adapted to further monitor, via the optical sensor, the aerosol until a stable post-event particle concentration is recorded, and wherein calibrating comprises combining a post-event optical sensor measurement with a post-event mass measurement.

5. The sensor system as claimed in claim 1, further comprising a sample intake device for operating during a sensing cycle to drive the aerosol being monitored towards a sensor element of the mechanical sensor.

6. The sensor system as claimed in claim 1, further comprising a particle filter arrangement for selecting a range of particle sizes for which the particle concentration is measured and the mass measurement is performed.

7. The sensor system as claimed in claim 1, further comprising a chemical sensor for providing information about the particle generating event.

8. The sensor system as claimed in claim 1, wherein the controller comprises a memory which stores a mapping between historical optical sensor measurements and corresponding historical mechanical sensor measurements.

9. An air treatment device, comprising a sensor system as claimed in claim 1.

10. A method of measuring aerosol particle concentration and mass concentration, comprising:
    monitoring, via a controller and an optical sensor, the aerosol by measuring a particle concentration and a particle size distribution;
    detecting, via the controller, a particle generating event based on the measured particle concentration and the particle size distribution, the particle generating event corresponding to a particular combination of particle concentration and particle size range information;
    performing, via the controller and a mechanical sensor, a mass measurement of collected particles only in response to detecting the particle generating event; and
    calibrating the optical sensor, via the controller, with use of the mass measurement.

11. The method as claimed in claim 10, wherein the mechanical sensor comprises a resonance frequency based mechanical sensor element, wherein the resonance frequency is dependent on a mass of particles deposited on the sensor element.

12. The method as claimed in claim 10, further comprising monitoring the aerosol, via the controller and the optical sensor, until a stable post-event particle concentration is recorded, wherein the calibrating comprises combining a post-event optical sensor measurement with a post-event mass measurement.

13. The method as claimed in claim 10, further comprising storing, via a memory, a mapping between historical optical sensor measurements and corresponding historical mechanical sensor measurements.

14. The method as claimed in claim 13, further comprising using the stored mapping to inhibit performing a mass measurement after detection of a particle generating event if there is a mapping to a historical mechanical sensor measurement.

15. The method as claimed in claim 14, further comprising scaling a stored historical mass measurement using the optical sensor measurement to provide a mass indication.

* * * * *